United States Patent [19]

Ku

[11] Patent Number: 4,981,849
[45] Date of Patent: Jan. 1, 1991

[54] ALPHA-ADRENERGIC RECEPTOR ANTAGONISTS

[75] Inventor: Thomas W. Ku, Dresher, Pa.

[73] Assignee: SmithKline Beecham Corporation, Philadelphia, Pa.

[21] Appl. No.: 315,370

[22] Filed: Feb. 23, 1989

[51] Int. Cl.$^5$ .................... A61K 31/55; C07D 487/00
[52] U.S. Cl. .................................... 514/215; 540/581
[58] Field of Search ......................... 540/815; 514/215

[56] References Cited

U.S. PATENT DOCUMENTS

| | | | |
|---|---|---|---|
| 3,833,591 | 9/1974 | McManus | 260/288 |
| 3,904,645 | 9/1975 | McManus | 260/326.5 B |
| 3,906,000 | 9/1975 | McManus | 260/326.5 B |
| 4,469,634 | 9/1984 | DeMarinis | 260/239 |
| 4,567,177 | 1/1986 | Biggi et al. | 540/581 |
| 4,769,368 | 9/1988 | Kaiser et al. | 514/217 |

FOREIGN PATENT DOCUMENTS 0030176 2/1981 Japan.
WO87/00522 1/1987 PCT Int'l Appl..

OTHER PUBLICATIONS

Hsu, J. of Pharmacology and Exp. Therapeutics, 214, 1981, pp. 188–192.
Cubeddu, American Heart J., 1988, pp. 133–162.
Hiebke, et al., Eur. J. of Pharmacology, 107(1985), 111–117.
Tsukamoto, et al., Biological Psychiatry, 19(9) 1984, 1283–1291.
Sanger, Psychopharmacology (1988) 95:413–7.
Brodstone, et al, Diabetes, 36, 1987, 932–7.
Galitzky, European J. of Clinical Investigation (1988), pp. 587–594.
Greenway et al., Clinical Therapeutics, 9(6), 1987, 663–9.

Primary Examiner—Mukund J. Shah
Assistant Examiner—E. C. Ward
Attorney, Agent, or Firm—Mary E. McCarthy; Stuart R. Suter; Edward T. Lentz

[57] ABSTRACT

Alpha-adrenoceptor antagonists having the formula:

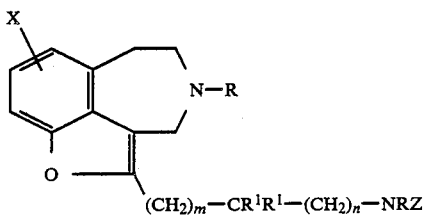

which are useful to produce $\alpha$-adrenoceptor antagonism, pharmaceutical compositions including these antagonists, and methods of using these antagonists to produce $\alpha$-adrenoceptor antagonism in mammals.

18 Claims, No Drawings

ALPHA-ADRENERGIC RECEPTOR ANTAGONISTS

FIELD OF THE INVENTION

This invention relates to novel substituted 2-aminoalkyl-3,4,5,6-tetrahydrofuro[4,3,2-ef][3]benzazepine compounds that are α-adrenergic receptor antagonists.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: α and β. Based upon selectivity of the receptors for a series of agonists and antagonists, the α adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, *J. Med. Chem.*, 25, 1389 (1982)). Experiments using 6-chloro-9-(3-methyl-2-butenyloxy)-3-methyl-2,3,4,5-tetrahydro-1H-3-benzazepine (SK&F 104078) demonstrated that the classical adrenoceptors are heterogeneous and can be divided into SK&F 104078—insensitive and SK&F 104078—sensitive $\alpha_2$ adrenoceptors. The latter variously are referred to as postjunctional $\alpha_2$ adrenoceptors or, preferably, $\alpha_3$ adrenoceptors, U.S. Pat. No. 4,683,229, Jul. 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with α adrenoceptors include methyldopa, clonidine, and prazosin. Efforts to modulate sympathetic tone through interactions with α adrenoceptors have resulted in several compounds that interact somewhat selectively with $\alpha_1$ or $\alpha_2$ adrenoreceptors. Selective agonists include phenylephrine and methoxamine which preferentially activate $\alpha_1$ receptors; and clonidine, α-methylnorepinephrine, and tramazoline which preferentially activate $\alpha_2$ adrenoceptors. Examples of selective α-adrenoceptor antagonists include prazosin which has high selectivity for $\alpha_1$ adrenoceptors; and the $\alpha_2$-selective blockers yohimbine and rauwolscine.

U.S. Pat. No. 4,469,634, describes allyloxy- and allylthio 2,3,4,5-tetrahydro-1H-3-benzazepines useful as intermediates for preparing $\alpha_2$ adrenoceptor affinity resins and as antihypertensive agents.

U.S. Pat. Nos. 3,833,591, 3,904,645, and 3,906,000 disclose substituted compounds of the following base structure:

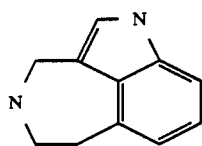

These compounds are disclosed as having utility as hypoglycemic agents.

PCT Application Number WO 87/00522 describes a series of 4-aminotetrahydrobenz[c,d]indoles and tetrahydroazepino-[3,4,5-c,d]indoles having the general formula:

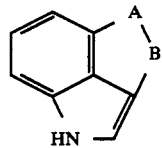

in which A—B is —CH$_2$—CH(NRR)—CH$_2$ or —CH$_2$—CH$_2$—NR—CH$_2$. These compounds are disclosed as having utility as dopamine agonists in the treatment of hypertension.

SUMMARY OF THE INVENTION

The present invention resides in the discovery that various substituted 2-aminoalkyl-3,4,5,6-tetrahydrofuro-[4,3,2-ef][3]benzazepine compounds are α-adrenoceptor antagonists. Presently preferred compounds of the invention include:

N-[(7-chloro-3,4,5,6-tetrahydro-4-methylfuro[4,3,2-ef][3]benzazepin-2-yl)methyl]-2-methylpropanesulfonamide;

7-chloro-3,4,5,6-tetrahydro-4-methylfuro[4,3,2-ef][3]benzazepine-2-methanamine;

N-[(7-chloro-3,4,5,6-tetrahydro-4-methylfuro[4,3,2-ef][3]benzazepin-2-yl)methyl]benzenepropanamide;

N-[(7-chloro-3,4,5,6-tetrahydro-4 -methylfuro[4,3,2--ef]-[3]benzazepin-2-yl)methyl]-2-phenoxyacetamide;

N-[(7-chloro 3,4,5,6-tetrahydro- 4-methylfuro-[4,3,2ef][3]benzazepin-2-yl)methyl]carbamic acid phenylmethyl ester;

N-[(7-chloro 3,4,5,6-tetrahydro-4 -methylfuro-[4,3,2-ef][3]benzazepin-2-yl)methyl]carbamic acid ethyl ester;

N-[(7-chloro-3,4,5,6-tetrahydro-4-methylfuro [4,3,2-ef][3]benzazepin-2 -yl)methyl]-N-methyl-carbamic acid ethyl ester;

N-[(7-chloro-3,4,5,6-tetrahydro-4-methylfuro[4,3,2-ef]-[3]benzazepin-2-yl)methyl]propanamide;

N-[(7-chloro-3,4,5,6-tetrahydro-4-methylfuro[4,3,2 -ef]-[3]benzazepin-2-yl)methyl]-N-methyl-propanamide; and N-[(7-chloro-3,4,5,6-tetrahydro-4-methylfuro-[4,3,2-ef][3]benzazepin-2-yl)methyl]benzamide.

In a further aspect of the invention there are provided methods of antagonizing α adrenoceptors in mammals, including humans, that comprise administering internally to a subject an effective amount of a substituted 2-aminoalkyl-3,4,5,6-tetrahydrofuro[4,3,2-ef][3]benzazepine compound.

Included in the present invention are pharmaceutical compositions that include compounds useful in the method of the invention and a suitable pharmaceutical carrier. Preferably, these compositions are used to produce α-adrenoceptor antagonism and contain an effective amount of compounds useful in the methods of the invention.

DETAILED DESCRIPTION OF THE INVENTION

The presently invented compounds that are α-adrenoceptor antagonists or are useful in preparing α-adrenoceptor antagonists are represented by the following Formula (I):

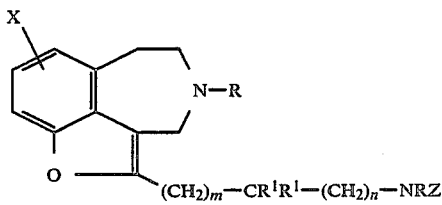

in which:
X is H, F, Cl, Br, I, $CF_3$, $C_{1-6}$ alkyl, $COR^2$, $CO_2R^2$, $CONR^3R^3$, CN, $NO_2$, $NR^4R^1$, $OR^4$, $SC_{1-4}$alkyl, $S(CH_2)_{0-6}$aryl, $SCF_3$, or any accessible combination thereof of up to three substituents;
each R independently is H, $C_{1-6}$alkyl, or $C_{3-5}$alkenyl, except where the double bond is in the 1-position;
each $R^1$ independently is H or $C_{1-6}$alkyl;
Z is R, $COR^5$, $CONR^3R^6$, $CO_2R^8$, or $SO_xR^7$;
m and n are each 0 to 2, but m+n is not greater than 2;
each $R^2$ independently is $C_{1-6}$alkyl or $(CH_2)_{0-6}$aryl;
each $R^3$ independently is H, $C_{1-6}$alkyl, or $(CH_2)_{0-6}$aryl;
each $R^4$ independently is H, $C_{1-6}$alkyl, $COR^2$ or $SO_2R^2$;
$R^5$ is H, , $C_{1-6}$alkyl, $(CH_2)_{0-6}$aryl, CH=CHaryl, $C_{3-5}$alkenyl, $(CH_2)_{1-3}$Oaryl, $(CH_2)_{1-3}$Saryl, or $(CH_2)_{1-3}OR^1$;
$R^6$ is H, $C_{1-6}$alkyl, $(CH_2)_{0-6}$aryl, $(CH_2)_{2-3}$Oaryl, $(CH_2)_{2-3}$Saryl, or $(CH_2)_{2-3}OR^1$;
$R^7$ is $C_{1-6}$alkyl, $(CH_2)_{0-6}$aryl, CH-32 CHaryl; $C_{3-5}$alkenyl, $(CH_2)_{1-3}$Oaryl, $(CH_2)_{1-3}$Saryl, or $(CH_2)_{1-3}OR^1$; and
$R^8$ is $C_{1-6}$ alkyl, $(CH_2)_{0-6}$aryl, $(CH_2)_{2-3}$Oaryl, $(CH_2)_{2-3}$Saryl, or $(CH_2)_{2-3}OR^1$; or a pharmaceutically acceptable salt thereof.

As used herein $C_{1-6}$alkyl means straight or branched alkyl of one to six carbon atoms, $C_{3-5}$alkenyl means a straight or branched chain alkenyl having from 3 to 5 carbon atoms, aryl means a phenyl group substituted by up to three X groups, and "accessible combination thereof" means any combination of up to three substituents on the phenyl moiety that is available by chemical synthesis and is stable.

Formula (Ia) includes presently preferred Formula (I) compounds:

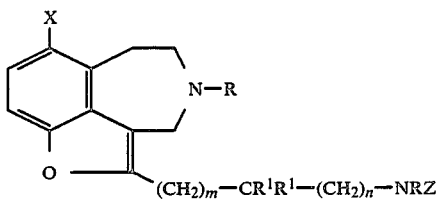

in which:
X is H, F, Cl, Br, I, $CF_3$, $C_{1-6}$alkyl, $COR^2$, $CO_2R^2$, $CONR^3R^3$, CN, $NO_2$, $NR^4R^1$, $OR^4$, $SC_{1-4}$alkyl, $S(CH_2)_{0-6}$aryl, $SCF_3$, or any accessible combination thereof of up to three substituents;
each R independently is H, $C_{1-6}$alkyl, or $C_{3-5}$alkenyl, except where the double bond is in the 1-position;
each $R^1$ independently is H or $C_{1-6}$alkyl;
Z is R, $COR^5$, $CONR^3R^6$, $CO_2R^8$, or $SO_2R^7$;
m and n are each 0 to 2, but m+n is not greater than 2;
each $R^2$ independently is $C_{1-6}$alkyl or $(CH_2)_{0-6}$aryl;
each $R^3$ independently is H, $C_{1-6}$alkyl, $COR^2$, or $SO_2R^2$;
each $R^4$ independently is H, $C_{1-6}$alkyl, $COR^2$, or $SO_2R^2$;
$R^5$ is H, $C_{1-6}$alkyl, $(CH_2)_{0-6}$aryl, CH=CHaryl, $C_{3-5}$alkenyl, $(CH_2)_{1-3}$Oaryl, $(CH_2)_{1-3}$Saryl, or $(CH_2)_{1-3}OR^1$;
$R^6$ is H, $C_{1-6}$ alkyl, $(CH_2)_{0-6}$aryl, $(CH_2)_{2-3}$Oaryl, $(CH_2)_{2-3}$Saryl, or $(CH_2)_{2-3}OR^1$;
$R^7$ is $C_{1-6}$alkyl, $(CH_2)_{0-6}$aryl, CH=CHaryl, $C_{3-5}$alkenyl, $(CH_2)_{1-3}$Oaryl, $(CH_2)_{1-3}$Saryl, or $(CH_2)_{1-3}OR^1$; and
$R^8$ is $C_{1-6}$alkyl, $(CH_2)_{0-6}$aryl, $(CH_2)_{2-3}$Oaryl, $(CH_2)_{2-3}$Saryl or $(CH_2)_{2-3}OR^1$; or a pharmaceutically acceptable salt thereof.

Compounds of Formula (I) are prepared by the synthetic pathways shown in Schemes I through III. In Schemes I through III, X is as defined in Formula (I).

SCHEME I

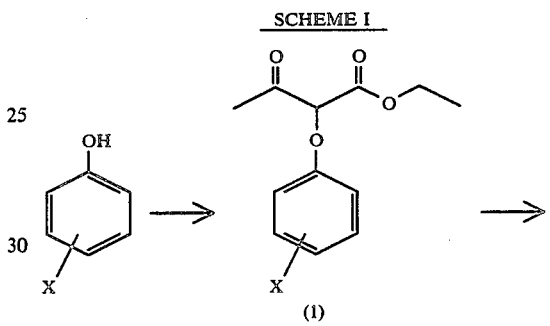

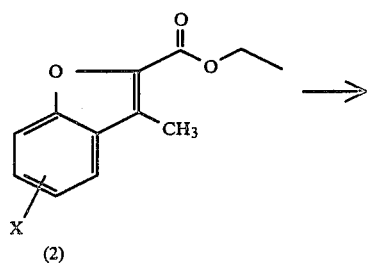

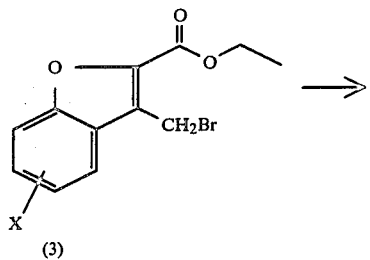

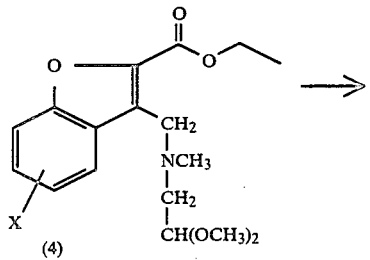

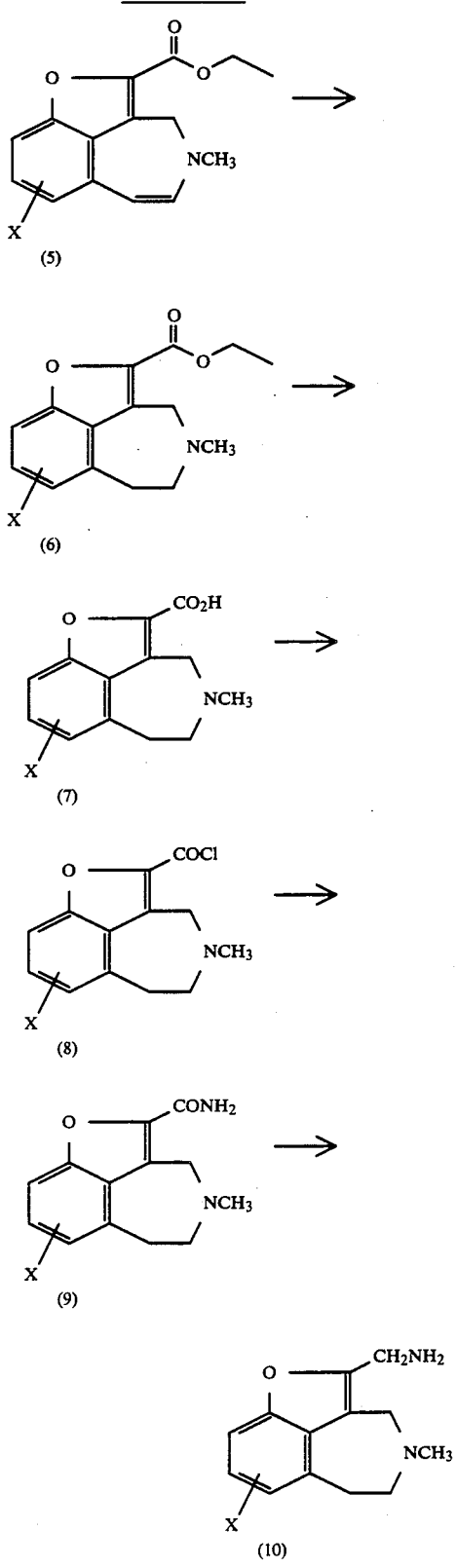

Scheme I shows the synthesis of Formula (I) compounds in which the 2-position substituent is $CH_2NH_2$. These compounds are α-adrenoceptor antagonists and they are also useful as intermediates in the synthesis of other Formula (I) compounds. In Scheme I, X is as defined in Formula (I) and the R group attached to the nitrogen of the azepine ring is represented by a methyl group.

According to Scheme I, phenol or a substituted phenol is treated with a base, such as sodium hydride, in a suitable organic solvent, such as toluene. The resulting sodium phenolates are heated at 40° C. to 120° C., preferably about 80° C., with an $C_{1-4}$alkyl 2-haloacetoacetate, preferably ethyl 2-chloroacetoacetate, to yield $C_{1-4}$alkyl 2-(phenoxy)acetoacetate compounds (1). Substituted benzofuran compounds (2) are prepared by treating formula (1) compounds with a strong acid, preferably sulfuric acid, at from −40° C. to 48° C., preferably about 0° C.

Formula (2) compounds are treated with a halogenating agent, preferably N bromosuccinimide (NBS), and an initiator, preferably dibenzoylperoxide, in an inert organic solvent, preferably carbon tetrachloride ($CCl_4$), preferably at reflux, to produce formula (3) compounds. Formula (4) compounds are prepared by dissolving formula (3) compounds in an organic solvent, such as acetone, and adding a suitable base, preferably potassium carbonate ($K_2CO_3$), and an N-($C_{1-6}$alkyl)-aminoacetaldehyde di($C_{1-4}$alkyl) acetal, preferably methylaminoacetaldehyde dimethyl acetal.

Formula (4) compounds are treated with acid, preferably trifluoromethanesulfonic acid in trifluoromethanesulfonic anhydride, to yield enamine compounds of formula (5). Formula (5) compounds are reduced with a reducing agent, preferably diborane, in an inert organic solvent, such as tetrahydrofuran, or catalytically to give benzazepine compounds of formula (6).

Thereafter, formula (6) compounds are hydrolyzed to formula (7) compounds with strong acid, preferably concentrated hydrochloric acid, in a suitable solvent, preferably acetic acid. These formula (7) compounds are converted to acid chlorides by treatment with a suitable reagent, such as thionyl chloride, to yield formula (8) compounds. Formula (8) compounds are reacted with an amine, such as concentrated ammonium hydroxide solution saturated with ammonia gas, to give formula (9) amide compounds. Formula (9) compounds are treated with a reducing agent, preferably diborane, in an inert organic solvent, such as tetrahydrofuran, to give benzazepine-2-methylamine compounds of formula (10).

SCHEME II

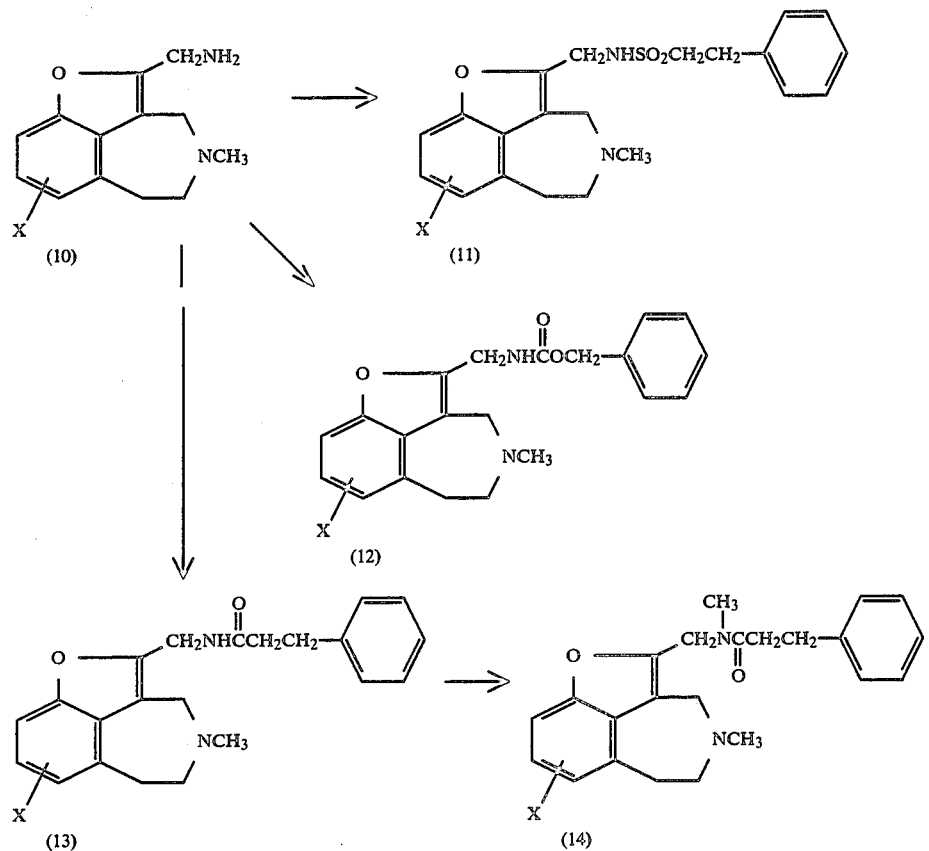

Scheme II shows the synthesis of Formula (I) compounds in which the 2-$CH_2NH_2$ moiety is substituted by a group Z, which is R, $COR^5$, $CONRR^6$, $CO_2R^2$ or $SO_2R^7$. In Scheme II, X is as defined in Formula (I), the R group attached to the nitrogen of the azepine ring is represented by a methyl group. According to Scheme II, compounds of the types exemplified by formulas (11), (12), and (13) can be obtained from formula (10) compounds.

Formula (11) compounds are prepared by reacting formula (10) compounds with an appropriately substituted sulfonyl chloride, such as styryl sulfonyl chloride, in the presence of a base, such as triethylamine, in an inert solvent, for example, tetrahydrofuran, to prepare the desired sulfonamide derivatives (11).

Formula (12) compounds are prepared from formula (10) compounds by treatment with a suitable haloformate, for example, benzyl chloroformate or ethyl chloroformate, in the presence of a base, such as triethylamine, in a suitable solvent, such as tetrahydrofuran.

Formula (13) compounds are prepared by reacting formula (10) compounds with an acid chloride, for example hydrocinnamoyl chloride or propionyl chloride, in the presence of a base, such as triethylamine, in an inert solvent, such as tetrahydrofuran.

Formula (11), (12), and (13) compounds are elaborated further to produce compounds which are more highly substituted on the nitrogen of the 2-$CH_2NH_2$ group. Formula (14) compounds are an example of this group of compounds. These products are formed when a formula (13) compound is alkylated by a $C_{1-6}$alkyl halide or a $C_{3-5}$alkenyl halide, such as methyliodide or allyl iodide, in the presence of a base, such as sodium hydride, in a suitable solvent, such as dimethylformamide.

SCHEME III

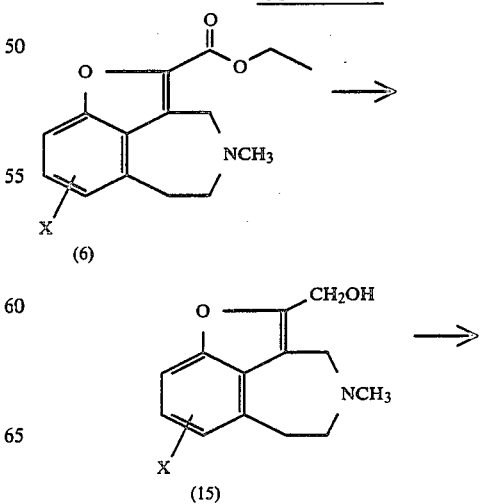

-continued
SCHEME III

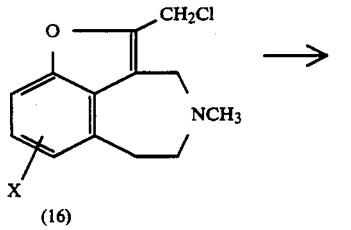

(16)

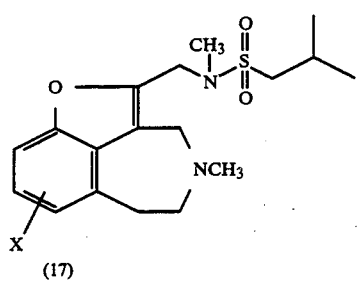

(17)

Scheme III shows an alternate route to the preparation of substituted 2-(sulfonamido)methyl Formula (I) compounds, which are Scheme II, formula (11) compounds. In Scheme III, X is as defined in Formula (I) and the R roup attached to the nitrogen of the azepine ring is represented by a methyl group.

According to Scheme III, formula (6) compounds are added to a suitable reducing agent, preferably lithium aluminum hydride (LAH) and aluminum chloride, in an inert solvent, such as ethyl ether, to yield formula (15) compounds. Formula (16) compounds are prepared from formula (15) compounds by treatment with a suitable halogenating agent, such as thionyl chloride, in an inert solvent, such as methylene chloride. The halide in formula (16) compounds is displaced by an appropriately substituted sulfonamide, such as N,2 dimethyl-1-propanesulfonamide (synthesis described in U.S. Pat. No. 4,454,139), in the presence of a base, preferably sodium hydride, in a suitable solvent, such as dimethylformamide, to give formula (17) compounds.

Schemes I through III outline preparation of Formula (I) compounds in which R is methyl. Formula (I) compounds wherein R is other than methyl are formed by selecting the N-($C_{1-6}$alkyl)aminoacetaldehyde di($C_{1-4}$alkyl)acetal used in preparing the formula (4) compounds of Scheme I so that the nitrogen is desirably substituted. Alternatively, Formula (I) compounds wherein R is other than methyl are prepared by reacting a Formula (I) compound wherein R is methyl with an alkyl haloformate, preferably trichloroethyl chloroformate, at approximately 50° C. to 100° C. to produce a trihaloalkyl carbamate. To this carbamate dissolved in a suitable organic solvent, such as tetrahydrofuran, is added an acid, preferably acetic acid, and a reducing agent, such as zinc dust, to yield a product in which R is hydrogen. This subsequently is reacted with a halo-$R^8$ compound, wherein $R^8$ is $C_{2-6}$alkyl or $C_{3-5}$alkenyl, to yield Formula (I) compounds wherein R is $C_{2-6}$alkyl or $C_{3-5}$alkenyl, respectively.

The substituted phenols and $C_{1-4}$alkyl 2-haloacetoacetates used as starting materials in Scheme I are commercially available or can be synthesized from available materials by known methods. Additionally, the reactants used in Schemes I through III are available or can be synthesized from available materials by known methods.

The pharmaceutically acceptable, nontoxic, acid addition salts having the utility of the free bases of Formula (I), are formed with inorganic or organic acids, by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p aminobenzoic, glutamic, benzenesulfonic, hydrochloric, hydrobromic, sulfuric, cyclohexylsulfamic, phosphoric and nitric acids.

Because the compounds of Formula (I) are α-adrenoceptor antagonists they are useful in treating cardiovascular diseases in which changes in vascular resistance are desirable, including hypertension, pulmonary hypertension, congestive heart failure, myocardial ischemia, angina pectoris, and peripheral vascular disease. Formula (I) compounds also are useful in treating benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The α-adrenoceptor activity of certain compounds of the present invention was determined using the following in vitro systems.

Alpha$_1$ adrenoceptor antagonist activity was determined using the rabbit aorta. Male New Zealand White rabbits (2–4 Kg) were euthanized by cervical concussion. A 4 cm portion of the thoracic aorta was removed and placed in a dish of cold (10° C.) Krebs Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force-displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6 μM) to block neuronal uptake and propranolol (1 82 M) to block beta-adrenoceptors. Tissues were usually challenged once with norepinephrine (0.1 μM) during the equilibration period to check for viability.

A cumulative concentration response curve to norepinephrine was obtained in each aortic segment. Following washout of norepinephrine, the α adrenoceptor antagonist to be tested was added to the bath. After the tissue had been in contact with the antagonist for 30–60 minutes, the norepinephrine concentration response curve was repeated in the presence of antagonist. The tissue was then washed again, and a tenfold higher concentration of antagonist added. Following equilibration (30–60 minutes), a third norepinephrine concentration-response curve was determined in the presence of the antagonist.

The receptor dissociation constant for the ($K_B$) for the antagonist was determined using the relationship $$K_B = \frac{\text{Antagonist Concentration}}{\text{Dose Ratio} - 1}$$

(Furchgott, R. F., *Handbook of Experimental Pharmacology*, eds. Eichler, et al., pp. 283–335 (Springer 1972)). The $K_B$ value obtained at each antagonist concentration was averaged to obtain a mean KB for each experiment.

Alpha$_2$ adrenoceptor antagonist activity of the compounds was determined using the isolated, superfused guinea pig left atrium. Briefly, the heart is removed from a pentobarbital anesthetized male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration-response curve for B-HT 920 (a known $\alpha_2$ agonist) is prepared by administering increasing concentrations of B-HT 920 following each successive stimulation. The tissue then is superfused for thirty minutes with the α-adrenoceptor antagonist to be tested and the B-HT 920 concentration-effect curve is repeated in the presence of antagonist. Data are reported as $K_B$, defined above. Additional details of this test system are found in Hieble, J. P. and R. G. Pendleton, *Arch. Pharmacol.*, 309:217–224 (1979).

Alpha$_3$ adrenoceptor antagonist receptor activity was determined using the dog saphenous vein (DSV) as the test system. This test system has been shown a suitable preparation in which to characterize postsynaptic $\alpha_2$ ($\alpha_3$) adrenoceptors, Sullivan, A. T. and G. M. Drew, *Arch. Pharmacol.*, 314:249–58 (1980). This test system is prepared by removing the lateral saphenous vein from an anesthetized dog and cutting the vein into segments of 4 mm in length. Segments are mounted as described for the isolated rabbit aorta.

The $\alpha_3$ adrenoceptor antagonist activity of the compounds of interest is determined by measuring shifts in the dose response curve of a specific agonist induced by the tested compounds. The $\alpha_2$, $\alpha_3$ agonist, B-HT 920, was used in testing the compounds listed in Table I.

Representative Formula (I) compounds which were tested using the above described in vitro test systems are listed in Table 1. Each of the compounds tested was found to have antagonist activity at one or more of the α-adrenoceptor subtypes.

Table 1

N-[(7-chloro-3,4,5,6-tetrahydro-4-methylfuro[4,3,2-ef][3]benzazepin-2-yl)methyl]-2-methylpropanesulfonamide;

7-chloro-3,4,5,6-tetrahydro-4-methylfuro[4,3,2-ef]-[3]benzazepine-2-methanamine;

N-[(7-chloro-3,4,5,6-tetrahydro-4-methylfuro[4,3,2 -ef]-[3]benzazepin-2-yl)methyl]benzenepropanamide;

N-[(7-chloro-3,4,5,6-tetrahydro-4-methylfuro[4,3,2-ef][3]benzazepin-2-yl)methyl]-2-phenoxyacetamide;

N-[(7-chloro-3,4,5,6-tetrahydro-4-methylfuro-[4,3,2-ef]]4,3,2-ef][3]benzazepin-2-yl)methyl]carbamic acid phenylmethyl ester;

N-[(7-chloro-3,4,5,6-tetrahydro-4-methylfuro-[4,3,2-ef][3]benzazepin-2-yl)methyl]carbamic acid ethyl ester;

N-[(7 chloro-3,4,5,6-tetrahydro-4-methylfuro[4,3,2-ef][3]benzazepin-2-yl)methyl]-N-methyl-carbamic acid ethyl ester;

N-[(7-chloro-3,4,5,6-tetrahydro-4-methylfuro[4,3,2-ef][3]benzazepin-2-yl)methyl]propanamide;

N-[(7-chloro-3,4,5,6-tetrahydro-4-methylfuro[4,3,2-ef][3]benzazepin-2-yl)methyl]-N-methyl-propanamide; and N-[(7-chloro-3,4,5,6-tetrahydro-4-methylfuro-[4,3,2-ef][3]benzazepin-2-yl)methyl]benzamide.

The antihypertensive activity of certain compounds of the present invention was determined using the spontaneously hypertensive rat model. The details of this in vivo test are found in Roesler, J. M., et al., *J. Pharmacol. Exp. Ther.*, 236:1–7 (1986).

Novel pharmaceutical compositions are obtained when the compounds are incorporated with pharmaceutical carriers into convenient dosage forms such as capsules, tablets, or injectable preparations. Standard solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax.. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing. when necessary, for tablet forms, or mixing, filling, and . dissolving the ingredients, as appropriate, to give the desired oral or parenteral products.

Doses of the present compounds in pharmaceutical dosage units will be an efficacious, nontoxic quantity selected from the range of 0.01–100 mg/kg of active compound, preferably 0.1–50 mg/kg. The selected dose is administered to a human patient in need of treatment from 1–4 times daily, orally, rectally, topically, by inhalation, or injection, or continuously by infusion. Oral administration, however, is preferred because it is more convenient for the patient.

The following examples are illustrative of preparation of Formula (I) compounds. The examples are not intended to limit the scope of the invention as defined hereinabove and as claimed below.

EXAMPLE 1

Ethyl 7-Chloro-3,4,5,6-tetrahydro- 4 -methylfuro-[4,3,2-ef][3]benzazepine-2-carboxylate (i) Ethyl 2 -(4-Chlorophenoxy)acetoacetate A 60% dispersion of sodium hydride in mineral oil (40 g, 1 mol) was washed with dry petroleum ether and suspended in dry toluene (700 ml). The suspension was stirred under argon and carefully treated with a solution of 4-chlorophenol (128.6 g, 1 mol) in dry toluene (300 ml) added dropwise. The resulting suspension was stirred for 1 hour, warmed to 80° C. and treated with ethyl 2-chloroacetoacetate (165 g, 1 mol) added dropwise to maintain the internal temperature between 80°–85° C. The resulting solution was stirred at 80° C.

for 4 hours, cooled and carefully treated with ice. The organic phase was washed with water (3×200 ml), 10% sodium hydroxide (2×75 ml), 75 ml), water (20 ml) and brine (100 ml), dried with magnesium sulfate, filtered and concentrated. The resulting oil was distilled in vacuo [bp 126°-132° C. (0.1 mm)]to give 95 g (37%) of ethyl 2-(4-chlorophenoxy)-acetoacetate.

(ii) Ethyl 5-Chloro-3-methyl-2-benzofurancarboxylate: mp 112°-114° C.

Ethyl 2-(4-chlorophenoxy)acetoacetate (90.3 g, 0.353 mol) was added dropwise to sulfuric acid (240 ml) stirred at 0° C. The resulting suspension was stirred at 0° C for 3.5 hours, poured onto crushed ice and the mixture stirred for 0.5 hours. The mixture was extracted with toluene and the organic phase was washed with 5% sodium bicarbonate and water. The organic phase was dried with magnesium sulfate, filtered and concentrated. The crude product was recrystallized from cyclohexane to give 54.5 g (65%) of ethyl 5-chloro-3-methyl-2-benzofurancarboxylate: mp 80°-82° C.

(iii) Ethyl 3-Bromomethyl-5-chloro-2-benzofurancarboxylate

A mixture of ethyl 5-chloro-3-methyl-2 -benzofurancarboxylate (52.5 g, 0.22 mol), N-bromosuccinimide (39.15 g, 0.22 mol) and benzoyl peroxide (0.4 g) in carbon tetrachloride (750 ml) was stirred and refluxed for 10 hours. The mixture was cooled, filtered and the filtrate was concentrated. The crude product was recrystallized from hexane to give 52.8 g (76%) of ethyl 3-bromomethyl-5-chloro-2-benzofurancarboxylate: mp 112-114° C.

(iv) Ethyl 5-Chloro-3-[N-(2,2-dimethoxyethyl)-N-methyl (aminomethyl)]-2-benzofurancarboxylate A mixture of ethyl 3-bromomethyl-5-chloro-2-benzofurancarboxylate (52.75 g, 0.166 mol), methylaminoacetaldehyde dimethyl acetal (19.0 g, 0.167 mol) and potassium carbonate (45 g) in dry acetone (600 ml) was stirred under argon for 30 hours, filtered and the filtrate evaporated. The residue was partitioned between ethyl ether and water and the organic phase was dried with magnesium sulfate, filtered, and concentrated to give ethyl 5-chloro-3-[N-(2,2 dimethoxyethyl)-N methyl(aminomethyl)]-2 -benzofurancarboxylate: mp 58°-60° C.

(v) Ethyl 7-Chloro-3,4-dihydro-4-methylfuro-[4,3,2 -ef][3]benzazepine-2-carboxylate Ethyl 5-chloro-3-[N-(2,2 dimethoxyethyl)-N-methyl-(aminomethyl)]-2-benzofurancarboxylate (8.5 g, 24 mmol) was added to a mixture of trifluoromethanesulfonic anhydride (3 ml) and trifluoromethanesulfonic acid (30 ml), stirred under argon in a water bath, dropwise over 10 minutes to maintain the internal temperature between 25°-30° C. The mixture was stirred for 0.5 hours, poured into a stirred mixture of ethyl ether (750 ml) and ice water (200 ml) and the aqueous phase was carefully basified with potassium carbonate to pH 9.5. The phases were separated and the aqueous phase was extracted with ethyl ether (2×200 ml). The organic phases were combined, dried with magnesium sulfate, filtered and concentrated to give ethyl 7-chloro-3,4-dihydro-4-methylfuro[4,3,2-ef][3]benzazepine-2-carboxylate.

(vi) Ethyl 7-Chloro-3,4,5,6-tetrahydro-4-methylfuro[4,3,2-ef][3]benzazepine-2-carboxylate A solution of ethyl 7-chloro-3,4-dihydro-4-methylfuro[4,3,2-ef][3]benzazepine-2-carboxylate in dry tetrahydrofuran (50 ml) was added to borane in tetrahydrofuran (1 M, 100 ml, 0.1 mol) and stirred under on at 0° C. The resulting solution was refluxed for 3.5 hours, cooled, carefully treated with ethanol and evaporated. The residue was refluxed in absolute ethanol (125 ml) for 1.5 hours and concentrated. The residual oil was stirred with ethyl ether (500 ml) and the mixture was filtered. The filtrate was treated with hydrogen chloride and the resulting solid was recrystallized from ethanol to give ethyl 7-chloro-3,4,5,6-tetrahydro-4-methylfuro-[4,3,2-ef][3]benzazepine-2-carboxylate hydrochloride; mp 24420 -247° C.

EXAMPLE 2

7-Chloro-3,4,5,6-tetrahydro-4-methylfuro-[4,3,2-ef][3]benzazepine-2-carbonyl Chloride A mixture of ethyl 7-chloro-3,4,5,6-tetrahydro-4-methylfuro[4,3,2-ef][3]benzazepinecarboxylate (5.2 g, 17.5 mmol), prepared as in Example 1, in glacial acid (82 ml) and 6 N hydrochloric acid was refluxed with stirring for 5 hours. The mixture was concentrated in vacuo at 50° C. and azeotroped with toluene to give the carboxylic acid hydrochloride as a solid, which was refluxed in thionyl chloride (500 ml) for 2.5 hours. The reaction solution was concentrated to remove the thionyl chloride and the residue was azeotroped with methylene chloride to give 7-chloro-3,4,5,6-tetrahydro-4-methylfuro[4,3,2-ef]-3]benzazepine-2-carbonyl chloride (6 g, 100%).

EXAMPLE 3

7-Chloro-3,4,5,6-tetrahydro-4-methylfuro[4,3,2-ef]-[3]benzazepine-2-carboxamide

To a mixture of 7-chloro-3,4,5,6-tetrahydro-4-methylfuro[4,3,2-ef][3]benzazepine-2-carbonyl chloride (5 g, 15.6 mmol), prepared as in Example 2, in tetrahydrofuran (200 ml) in a dry ice/acetbne bath was bubbled anhydrous ammonia gas for 15 minutes. The mixture was allowed to stir at room temperature for 2 hours and concentrated. The residue was triturated with 10% sodium hydroxide solution (5 ml) and filtered to give 7 chloro-3,4,5,6-tetrahydro-4-methylfuro [4,3,2-ef][3]benzazepine-2-carboxamide (3.2 g, 78%, mp 230° C).

EXAMPLE 4

7-Chloro 3,4,5,6-tetrahydro-N,N,4-trimethylfuro[4,3,2-ef]-[3]benzazepine-2-carboxamide To a mixture of 7-chloro-3,4,5,6-tetrahydro-4-methylfuro[4,3,2-ef][3]benzazepine-2-carbonyl chloride, prepared as in Example 2, (0.2 g, 0.62 mmol) in methylene chloride (30 ml) at 0° C. was bubbled dimethylamine for 5 minutes. The resulting solution was stirred for 1 hour, washed with 10% sodium hydroxide solution, and dried over nesium sulfate. Removal of the solvent gave 7-chloro-3,4,5,6-tetrahydro-N,N,4-trimethylfuro[4,3,2-ef]-[3]benzazepine-2-carboxamide (0.15 g, 82%).

EXAMPLE 5

7-Chloro-3,4,5,6-tetrahydro-4-methylfuro[4,3,2-ef]-[3]benzazepine-2-methanamine

To a solution of 7-chloro-3,4,5,6-tetrahydro-4-methylfuro[4,3,2-ef][3]benzazepine-2-carboxamide (2.5 g, 9.4 mmol), prepared as in Example 3, in tetrahydrofuran (20 ml) was added diborane (10 ml, 10 mmol). The mixture was refluxed for 3 hours, then treated with methanol (10 ml) and dilute hydrochloric acid (10 ml).

The mixture was refluxed for 30 minutes and allowed to stir at room temperature overnight. The product as a white hydrochloride salt precipitated out of the mixture to give 7-chloro-3,4,5,6-tetrahydro-4-methylfuro[4,3,2-ef]-[3]benzazepine-2-methanamine (2.3 g, 73%, mp 230° C.).

EXAMPLE 6

N-[(7-Chloro-3,4,5,6-tetrahydro-4-methylfuro[4,3,2-ef]-[3]benzazepin-2-yl)methyl]benzenepropanamide To a solution of 7-chloro-3,4,5,6-tetrahydro-4-methylfuro[4,3,2-ef][3]benzazepine-2-methanamine hydrochloride (0.5 g, 2.0 mmol), prepared as in Example 5, and triethylamine (1.1 ml, 7.9 mmol) in tetrahydrofuran (6 ml) at 0°-5° C. was added dropwise over 5 minutes a solution of hydrocinnamoyl chloride (0.3 ml, 1.98 mmol). The reaction mixture was stirred in the ice-bath for 30 minutes and quenched with ice-cold 5% sodium bicarbonate solution (80 ml). The product was extracted into ethyl acetate. Evaporation of the extract gave crude product (0.6 g, 79%). Chromatography on silica (4% methanol in methylene chloride) yielded 0.42 g of N-[(7-chloro-3,4,5,6-tetrahydro4-methylfuro [4,3,2-ef][3]benzazepin-2-yl)methyl]benzenepropanamide (mp 141°-143° C.).

EXAMPLE 7

N-[(7-Chloro-3,4,5,6-tetrahydro-4-methylfuro[4,3,2-ef]-[3]benzazepin-2-yl)methyl]-2-phenoxyacetamide To a suspension of 7-chloro-3,4,5,6-tetrahydro-4-methylfuro[4,3,2-ef][3]benzazepine-2-methanamine hydrochloride (0.57 g, 1.77 mmol), prepared as in Example 5, and triethylamine (1 ml) in tetrahydrofuran (25 ml) in an ice bath was added dropwise phenoxyacetyl chloride (0.28 ml, 2.0 mmol). After removing the ice-bath, the mixture was allowed to stir overnight at room temperature, quenched with ice water, and extracted with ethyl ether. The combined extracts were dried over magnesium sulfate and evaporated to give ah oil (0.3 g, 44%), which was flash chromatographed an silica gel, eluting with 3% methanol in methylene chloride. The residue was triturated with isopropanol to give N-[(7-chloro-3,4,5,6tetrahydro-4-methylfuro [4,3,2-ef][3]benzazepine-2-yl)methyl]-2-phenoxyacetamide (mp 126°-127° C.).

EXAMPLE 8

N-[(7 Chloro-3,4,5,6-tetrahydro-4-methylfuro-[4,3,2-ef][3]benzazepin-2-yl)methyl]carbamic Acid Phenylmethyl Ester To a solution of 7-chloro-3,4,5,6-tetrahydro-4-methylfuro [4,3,2-ef[3]benzazepine-2-methanamine hydrochloride (0.5 g, 2.0 mmol), prepared as in Example 5, and triethylamine (1.1 ml) in tetrahydrofuran (6.0 ml) in an ice-bath was added dropwise over 4 minutes a solution of benzyl chloroformate (0.29 ml, 1.93 mmol) in tetrahydrofuran (2 ml). The reaction mixture was stirred for 40 minutes, quenched with cold 5% sodium bicarbonate solution (80 ml), and extracted with ethyl acetate. The combined extracts were washed with saturated sodium chloride solution, dried over sodium sulfate and evaporated to give a brown oil (0.73 g), which was flash chromatographed on silica gel, eluting with 2% methanol in methylene chloride, to give N-[(7-chloro-3,4,5,6-tetrahydro-4methylfuro [4,3,2-ef][3]benzazepin-2-yl) methyl]carbamic acid phenylmethyl ester (0.27 g, 37%, mp 112°-115° C.).

EXAMPLE 9

N-[(7-Chloro-3,4,5,6-tetrahydro-4-methylfuro-[4,3,2-ef]3]benzazepin-2-yl)methyl]carbamic Acid Ethyl Ester To a magnetically stirred solution of 7-chloro-3,4,5,6-tetrahydro-4-methylfuro[4,3,2-ef][3]-benzazepine-2-methanamine hydrochloride (0.74 g, 3.0 mmol), prepared as in Example 5, and triethylamine (1.7 ml) in tetrahydrofuran (10 ml) at 5° C. was added slowly ethyl chloroformate (0.3 ml, 3.0 mmol). After 0.5 hours, the mixture was quenched with 5% sodium bicarbonate solution (100 ml) and extracted with ethyl acetate (2×50 ml) The combined organic extracts were washed with water and saturated sodium chloride solution, dried over magnesium sulfate, and evaporated to give a brown solid (0.83 g, 86%). The crude product was purified by flash chromatography on silica gel, eluting with 3.5% ethanol in methylene chloride, to give N-[(7-chloro-3,4,5,6-tetrahydro-4-methylfuro [4,3,2-ef][3]benzazepin-2yl)-methyl carbamic acid ethyl ester (mp 149°-151° C.).

EXAMPLE 10

N-[(7-Chloro-3,4,5,6-tetrahydro-4-methylfuro-[4,3,2-ef][3]benzazepin-2-yl)methyl]-N-methyl-carbamic Acid Ethyl Ester A solution of N-[(7-chloro-3,4,5,6-tetrahydro-4-methylfuro-[4,3,2-ef][3]benzazepin-2-yl)methyl]carbamic acid ethyl ester (0.67 g, 2.1 mmol), prepared as in Example 9, in dimethylformamide (6 ml) was treated with sodium hydride (50% dispersed in oil, 0.2 g, 4.2 mmol) at 0° C. A solution of iodomethane (0.14 g, 2.2 mmol) in dimethylformamide (1 ml) was then added. The resulting mixture was stirred in the ice bath for 15 minutes, quenched with a cold 5% sodium bicarbonate solution (100 ml), and extracted with a solution of ethyl acetate and hexane (75/15=v/v, 2×50 ml). The combined extracts were washed with water (2×15 ml) and saturated sodium chloride solution (1×15 ml), dried over magnesium sulfate, and evaporated to give an oil (0.69 g, 84%). Flash chromatography (on silica gel, eluting with 1% ethanol in ethyl acetate) gave N [(7-chloro-3,4,5,6-tetrahydro-4-methylfuro [4,3,2-ef][3]benzazepin-2-yl)methylcarbamic acid ethyl ester (0.32 g, mp 199°-200° C.).

EXAMPLE 11

N-[(7-Chloro-3,4,5,6-tetrahydro-4-methylfuro[4,3,2-ef]-[3]benzazepin-2-yl)methyl]propanamide To a magnetically stirred solution of 7-chloro-3,4,5,6-tetrahydro-4-methylfuro [4,3,2-ef][3]benzazepine-2-methanamine hydrochloride (0.8 g, 3.2 mmol), prepared as in Example 5, and triethylamine (1.8 ml, 12.4 mmol) in tetrahydrofuran (12 ml) at 5° C. was added slowly a solution of propionyl chloride (0.29 ml, 3,28 mmol) in tetrahydrofuran (3 ml) at 5° C. The resulting mixture was stirred for 1 hour, poured into a cold solution of sodium bicarbonate, and extracted with ethyl acetate. The combined extracts were washed with water, saturated sodium chloride solution, and dried over magnesium sulfate. The residue obtained after evaporation was purified by flash chromatography on silica gel, eluting with 3.5% methanol in methylene chloride, to give N-[(7-chloro-3,4,5,6-tetrahydro-4-methylfuro

[4,3,2-ef][3]benzazepin-2yl)methyl]-propanamide (0.7 g, 71%, mp 157.5°-160° C.).

EXAMPLE 12

N-[(7-Chloro-3,4,5,6-tetrahydro-4-methylfuro-[4,3,2-ef][3]benzazepin-2-yl)methyl]-N-methyl-propanamide To a stirred solution of N [(7-chloro-3,4,5,6-tetrahydro-4-methylfuro [4,3,2-ef][3]benzazepin-2-yl)-propanamide (0.42 g, 1.4 mmol), prepared as in Example 11, in dimethylformamide (8 ml) under argon was added sodium hydride dispersed in mineral oil (0.1 g, 2.3 mmol) at room temperature. After 15 minutes, the reaction mixture was cooled to 0° C. and a solution of iodomethane (0.1 ml, 1.3 mmol) was added over 5 minutes. The mixture was poured into a cold solution of sodium bicarbonate and saturated sodium chloride. The aqueous phase was extracted with ethyl acetate, dried over magnesium sulfate, and evaporated. Flash chromatography on silica gel, eluting with 4% ethanol in methylene chloride, gave 0.14 g (31%) of N [(7-chloro-3,4,5,6-tetrahydro-4-methylfuro[4,3,2-ef][3]benzazepin-2-yl)methyl]-N-methyl-propanamide (mp 195°-198° C.).

EXAMPLE 13

N-[(7-Chloro-3,4,5,6-tetrahydro-4-methylfuro[4,3,2-ef]-[3]benzazepin-2-yl)methyl]benzamide To a magnetically stirred solution of 7-chloro-3,4,5,6-tetrahydro-4-methylfuro [4,3,2-ef][3]benzazepine-2-methanamine hydrochloride (0.25 g, 1.0 mmol), prepared as in Example 5, and triethylamine (0.43 ml, 3.1 mmol) in methylene chloride (3 ml) at 5° C. was added slowly a solution of benzoyl chloride (0.15 ml, 1.3 mmol) in methylene chloride (2.5 ml) at 5° C. The resulting mixture was stirred for 2 hours at room temperature, poured into a cold solution of sodium bicarbonate (8 ml), and extracted with methylene chloride. The combined extracts were washed with water, saturated sodium chloride solution, and dried over magnesium sulfate. The residue (0.47 g) obtained after evaporation was purified by flash chromatography on silica gel, eluting with 3.5% methanol in methylene chloride, to give N-[(7-chloro-3,4,5,6-tetrahydro-4-methylfuro [4,3,2-ef][3]benzazepin-2-yl)methyl]-benzamide (0.15 g, 44%), which was converted to its hydrochloride salt (mp 135°-137° C.).

EXAMPLE 14

7-Chloro-3,4,5,6-tetrahydro-4-methylfuro[4,3,2-ef]-[3]benzazepine-2-methanol

To a suspension of anhydrous aluminum chloride (3.3 g, mmol) in anhydrous diethyl ether (280 ml) in an ice bath was added lithium aluminum hydride (2.7 g, mmol) in portions. The mixture was stirred at ice bath temperatures for 90 minutes and a solution of ethyl 7-chloro-3,4,5,6-tetrahydro-4-methylfuro[4,3,2-ef][3]-benzazepine-2-carboxylate (10 g, 34 mmol), prepared as in Example 1, in anhydrous diethyl ether (200 ml) was added over 45 minutes. The resulting white suspension was stirred for 50 minutes and water (4 ml), a solution of 10% sodium hydroxide (4 ml), and water (4 ml) were sequentially added carefully. The mixture was diluted with ether (500 ml) and filtered. The filtrate was evaporated to give 7 chloro-3,4,5,6-tetrahydro-4-methylfuro [4,3,2-ef][3]benzazepine-2-methanol (6.1 g, 72%).

EXAMPLE 15

2-Chloromethyl-7-chloro-3,4,5,6-tetrahydro-4-methylfuro[4,3,2-ef][3]benzazepine

To a suspension of 7-chloro-3,4,5,6-tetrahydro-4-methylfuro [4,3,2-ef][3]benzazepine-2-methanol (6.0 g, 24.0 mmol), prepared as in Example 14, in methylene chloride (150 ml) at 0° C. was added thionyl chloride (150 ml) over 15 minutes. The mixture was evaporated to give chloromethyl-7-chloro-3,4,5,6-tetrahydro-4-methylfuro - [4,3,2-ef][3]benzazepine hydrochloride (7.3 g, 99%).

EXAMPLE 16

N-[(Chloro-3,4,5,6-tetrahydro-4-methylfuro[4,3,2-ef]-[3]benzazepin-2-yl)methyl]-2-methylpropanesulfonamide To a magnetically stirred solution of N,2-dimethyl-1-propanesulfonamide (0.3 g, 2 0 mmol, U.S. Pat. No. 4,454,139) in dimethylformamide (6 ml) was added slowly a dispersion of sodium hydride (0.26 g, 5.31 mmol) in mineral oil. After the hydrogen gas evolution had subsided, 2-chloromethyl-7-chloro-3,4,5,6-tetrahydro-4-methylfuro [4,3,2-ef][3]benzazepine hydrochloride (0.42 g, 1.38 mmol), prepared as in Example 15, was added in portions. The resulting mixture was stirred for 1 hour at room temperature, poured into ice water (100 ml) and extracted with ethyl acetate. The combined extracts were washed with water, saturated sodium chloride solution, and dried over magnesium sulfate The residue (0.47 g) obtained after evaporation was purified by flash chromatography on silica gel, eluting with 0.3% ethanol in ethyl acetate, to give N-[(7-chloro-3,4,5,6-tetrahydro-4-methylfuro [4,3,2-ef][3]benzazepin-2-yl)methyl]-2-methylpropanesulfonamide (0.26 g, 48%, mp 101°-103° C.).

EXAMPLE 17

N-[(7-Chloro-3,4,5,6-tetrahydro-4-methylfuro [4,3,2-ef][3]benzazepin-2-yl)methyl]-2-phenylethenesulfonamide To a magnetically stirred solution of 7-chloro-3,4,5,6-tetrahydro-4-methylfuro [4,3,2-ef][3]benzazepine-2-methanamine hydrochloride (1.5 mmol), prepared as in Example 5, and triethylamine (2.5 ml) in tetrahydrofuran (25 ml) at 5° C. is added slowly a solution of styryl sulfonyl chloride (1.6 mmol) in tetrahydrofuran (2.5 ml). The resulting mixture is stirred for 2 hours at room temperature, poured into a cold solution of sodium bicarbonate (8 ml), and extracted with methylene chloride. The combined extracts are washed with water, dried over magnesium sulfate and concentrated to give N-[(7-chloro-3,4,5,6-tetrahydro-4-methylfuro[4,3,2-ef][3]-benzazepin-2-yl) methyl]-2-phenylethenesulfonamide.

EXAMPLE 18

N-[(7-Chloro-3,4,5,6-tetrahydro4-methylfuro [4,3,2-ef][3]benzazepin-2-yl)methyl]-2-benzeneethanesulfonamide Using the general procedure of Example 17, replacing styryl sulfonyl chloride with 2 phenethyl sulfonyl chloride gives N-[(7-chloro-3,4,5,6-tetrahydro-4-methylfuro [4,3,2-ef][3]benzazepin-2-yl)methyl]-2-benzeneethanesulfonamide.

EXAMPLE 19

N-[(7-Chloro-3,4,5,6-tetrahydro-4-methylfuro [4,3,2-ef][3]benzazepin-2-yl)methyl]-2-benzenesulfonamide Using the general procedure of Example 17, replacing styryl sulfonyl chloride with benzene sulfonyl chloride gives N-[(7-chloro-3,4,5,6-tetrahydro-4-methylfuro-[4,3,2-ef][3]benzazepin-2-yl)methyl]-2-benzenesulfonamide.

EXAMPLE 20

7-Methyl-3,4,5,6-tetrahydro-4-methylfuro [4,3,2-ef][3]-benzazepine-2-methanamine Using the general procedure of Example 1, replacing chlorophenol with 4 methylphenol gives ethyl 7-methyl-3,4,5,6-tetrahydro-4-methylfuro [4,3,2-ef][3]benzazepine-2-carboxylate.

Using the general procedures of Examples 2, 3, and 5, the ethyl 7-methyl-carboxylate is de-esterified with hydrochloric acid in acetic acid, converted to an acid chloride with thionyl chloride, aminated with ammonia gas, and reduced with diborane to give 7-methyl-3,4,5,6-tetrahydro-4-methylfuro [4,3,2-ef][3]benzazepine-2-methanamine.

EXAMPLE 21

N-[(7-Methyl-3,4,5,6-tetrahydro-4-methylfuro [4,3,2-ef]-[3]benzazepin-2-yl)methyl]benzenepropanamide Using the general procedure of Example 6, replacing 7-chloro-3,4,5,6-tetrahydro-4-methylfuro[4,3,2-ef][3]benzazepine-2-methanamine with 7-methyl-3,4,5,6-tetrahydro-4-methylfuro [4,3,2-ef][3]benzazepine-2-methanamine, prepared as in Example 20, gives N-[(7-methyl-3,4,5,6-tetrahydro-4-methylfuro [4,3,2-ef][3]benzazepin-2-yl)methyl]benzenepropanamide.

EXAMPLE 22

N-[(7-Methyl-3,4,5,6-tetrahydro-4-methylfuro -[4,3,2-ef][3]benzazepin-2-yl)methyl]carbamic Acid Phenylmethyl Ester Using the general procedure of Example 8, replacing 7-chloro-3,4,5,6-tetrahydro-4-methylfuro[4,3,2-ef][3]-benzazepine-2-methanamine with 7-methyl-3,4,5,6-tetrahydro-4-methylfuro [4,3,2-ef][3]benzazepine-2-methanamine, prepared as in Example 20, gives N-[(7-methyl-3,4,5,6-tetrahydro-4-methylfuro [4,3,2-ef][3]benzazepin-2-yl)methyl]carbamic acid phenylmethyl ester.

EXAMPLE 23

N-[(7-Methyl-3,4,5,6-tetrahydro-4-methylfuro [4,3,2-ef][3]benzazepin-2-yl)methyl]-2-phenylethenesulfonamide Using the general procedure of Example 17, replacing 7-chloro-3,4,5,6-tetrahydro-4-methylfuro[4,3,2-ef][3]benzazepine-2-methanamine with 7-methyl-3,4,5,6-tetrahydro-4-methylfuro [4,3,2-ef][3]benzazepine-2-methanamine, prepared as in Example 20, gives N-[(7-methyl-3,4,5,6-tetrahydro-4-methylfuro [4,3,2-ef][3]benzazepin2-yl)methyl]-2-phenylethenesulfonamide.

EXAMPLE 24

9Chloro-3,4,5,6-tetrahydro-4-methylfuro[4,3,2-ef][3]-benzazepine-2-methanamine

Using the general procedure of Example 1, replacing 4-chlorophenol with 2-chlorophenol gives ethyl 9-chloro-3,4,5,6-tetrahydro-4-methylfuro [4,3,2-ef][3]benzazepine-2carboxylate.

Using the general procedures of Examples 2, 3, and 5, ethyl 9-chloro-3,4,5,6-tetrahydro-4-methylfuro[4,3,2-ef]-[3]benzazepine-2-carboxylate is de-esterified, converted to an acid chloride, aminated and reduced to give 9-chloro-3,4,5,6-tetrahydro-4-methylfuro[4,3,2-ef]-[3]benzazepine-2-methanamine.

EXAMPLE 25

N-[(9-Chloro-3,4,5,6-tetrahydro-4-methylfuro[4,3,2-ef]-[3]benzazepin-2-yl)methyl]benzenepropanamide Using the general procedure of Example 6, replacing 7-chloro-3,4,5,6-tetrahydro-4-methylfuro[4,3,2-ef][3]benzazepine-2-methanamine with 9-chloro-3,4,5,6-tetrahydro-4-methylfuro [4,3,2-ef][3]benzazepine-2-methanamine, prepared as in Example 24, gives N-[(9-chloro-3,4,5,6 -tetrahydro-4-methylfuro [4,3,2-ef][3]benzazepin-2-yl)methyl]benzenepropanamide.

EXAMPLE 26

N-[(9-Chloro-3,4,5,6-tetrahydro-4-methylfuro-[4,3,2-ef][3]benzazepin2-yl)methyl]carbamic Acid Phenylmethyl Ester Using the general procedure of Example 8, replacing 7-chloro-3,4,5,6-tetrahydro-4-methylfuro[4,3,2-ef][3]benzazepine-2-methanamine with 9-chloro-3,4,5,6-tetrahydro-4-methylfuro [4,3,2-ef][3]benzazepine-2-methanamine, prepared as in Example 24, gives N-[(9-chloro-3,4,5,6-tetrahydro-4-methylfuro [4,3,2-ef][3]benzazepin2-yl)methyl]carbamic acid phenylmethyl ester.

EXAMPLE 27

N-[(9-Chloro-3,4,5,6-tetrahydro-4-methylfuro-[4,3,2-ef][3]benzazepin2-yl)methyl]-2-phenylethenesulfonamide Using the general procedure of Example 17, replacing 7-chloro-3,4,5,6-tetrahydro-4-methylfuro[4,3,2-ef][3]benzazepine-2-methanamine with 9-chloro-3,4,5,6-tetrahydro-4-methylfuro[4,3,2-ef][3]benzazepine-2-methanamine, prepared as in Example 24, gives N-[(9-chloro-3,4,5,6-tetrahydro-4-methylfuro [4,3,2-ef][3]benzazepin-2-yl)-methyl]-2-phenylethenesulfonamide

EXAMPLE 28

7,9-Dichloro-3,4,5,6-tetrahydro-4-methylfuro[4,3,2-ef]-[3]benzazepine2-methanamine Using the general procedure of Example 1, replacing 4-chlorophenol with 2,4-dichlorophenol yields ethyl 7,9-dichloro-3,4,5,6-tetrahydro-4-methylfuro[4,3,2-ef][3]-benzazepine-2-carboxylate.

Using the general procedures of Examples 2, 3, and 5, ethyl 7,9-dichloro-3,4,5,6-tetrahydro-4-methylfuro [4,3,2-ef][3]benzazepine-2-carboxylate is de-esterified, converted to an acid chloride, aminated and reduced to give 7,9-dichloro3,4,5,6-tetrahydro-4-methylfuro[4,3,2-ef][3]benzazepine-2-methanamine.

EXAMPLE 29

N-[(7,9-Dichloro3,4,5,6-tetrahydro-4-methylfuro-[4,3,2-ef][3]benzazepin-2-yl)methyl]benzenepropanamide Using the general procedure of Example 6, replacing 7-chloro-3,4,5,6-tetrahydro-4-methylfuro[4,3,2-ef][3]benzazepine-2-methanamine with 7,9-dichloro-3,4,5,6-tetrahydro-4-methylfuro [4,3,2-ef[3]benzazepine-2-methanamine, prepared as in Example 28, gives N-[(7,9-dichloro-3,4,5,6-tetrahydro-4-methylfuro [4,3,2-ef][3]benzazepin-2-yl)methyl]benzenepropanamide.

EXAMPLE 30

N-[(7,9-Dichloro-3,4,5,6-tetrahydro-4-methyl-furo[4,3,2-ef][3]benzazepin-2-yl)methyl]carbamic Acid Phenylmethyl Ester Using the general procedure of Example 8, replacing 7-chloro-3,4,5,6-tetrahydro-4-methylfuro[4,3,2-ef][3]-benzazepine-2-methanamine with 7,9-dichloro-3,4,5,6-tetra-hydro-4-methylfuro [4,3,2-ef][3]benzazepin-2-methanamine, prepared as in Example 28, gives N-[(7,9-dichloro-3,4,5,6-tetrahydro-4-methylfuro [4,3,2-ef][3]benzazepin-2-yl )methyl]carbamic acid phenylmethyl ester.

EXAMPLE 31

N-[(7,9-dichloro-3,4,5,6-tetrahydro-4-methylfuro-[4,3,2-ef][3]benzazepin-2-yl)methyl]-2-phenylethenesulfonamide Using the general procedure of Example 17, replacing 8-chloro-3,4,5,6-tetrahydro-4-methylfuro[4,3,2-ef][3]benzazepine-2-methanamine with 7,9-dichloro-3,4,5,6-tetrahydro-4-methylfuro [4,3,2-ef][3]benzazepine-2-methanamine, prepared as in Example 28, gives N-[(7,9-dichloro-3,4,5,6-tetrahydro-4-methylfuro [4,3,2-ef][3]benzazepin-2-yl)methyl]-2-phenylethenesulfonamide.

EXAMPLE 32

7-Chloro-3,4,5,6-tetrahydro-4-methylfuro[4,3,2-ef]-[3]benzazepine-2-acetonitrile To an ice-cold solution of 2-chloromethyl-7-chloro-3,4,5,6-tetrahydro-4methylfuro [4,3,2-ef][3]benzazepine hydrochloride, prepared as in Example 15, (2.16 mmol) in dimethylsulfoxide (12 ml) is adde triethylamine (0.5 ml). Sodium cyanide (3.0 mmol) is then added in one portion. The resulting mixture is heated at 50° C. for 2 hours, and quenched with ice water (70 ml) and extracted with ethyl acetate. The combined extracts are washed with water, saturated sodium chloride solution, and dried over magnesium sulfate. The residue obtained after evaporation is purified by flash chromatography on silica to give 7-chloro-3,4,5,6-tetrahydro-4-methylfuro[4,3,2-ef][3]-benzazepine-2-acetonitrile.

EXAMPLE 33

7-Chloro-3,4,5,6-tetrahydro-4 methylfuro[4,3,2-ef][3]benzazepine-2-ethanamine

To a suspension of lithium aluminum hydride (176 mmol) in anhydrous diethyl ether (200 ml) and tetrahydrofuran (50 ml) in an ice-bath is added dropwise a solution of 7-chloro-3,4,5,6-tetrahydro-4-methyl-furo[4,3,2-ef][3]benzazepine-2-acetonitrile (44 mmol), prepared as in Example 33, in anhydrous diethyl ether (200 ml) and tetrahydrofuran (50 ml). The resulting suspension is stirred at reflux for 6 hours, and then, water (7 ml), a solution of 10% sodium hydroxide (7 ml), and water (21 ml) are added sequentially. The mixture is diluted with ether (500 ml) and filtered. The filtrate is evaporated to give 7-chloro-3,4,5,6-tetrahydro-4-methylfuro [4,3,2-ef][3]-benzazepine-2-ethanamine.

EXAMPLE 34

N-[2-(7-Chloro-3,4,5,6-tetrahydro-4-methylfuro[4,3,2-ef]-[3]benzazepin-2-yl)ethyl]benzeneethanesulfonamide To a solution of 7-chloro-3,4,5,6-tetrahydro-4-methylfuro [4,3,2-ef][3]benzazepine-2-ethanamine (1.5 mmol), prepared as in Example 34, and triethylamine (2.5 ml) in tetrahydrofuran (25 ml) at 5° C. is added slowly a solution of 2-phenethyl sulfonyl chloride (1.6 mmol) in tetrahydrofuran (2.5 ml). The resulting mixture is stirred for 2 hours at room temperature, poured into a cold solution of sodium bicarbonate (8 ml), and extracted with methylene chloride. The combined extracts are washed with water, saturated sodium chloride solution, and dried over magnesium sulfate. The residue obtained after evaporation is flash chromatographed to give N-[2-(7chloro-3,4,5,6-tetrahydro-4methylfuro [4,3,2-ef][3]benzazepin-2-yl)ethyl]benzeneethanesulfonamide.

EXAMPLE 35

7-Chloro-3,4,5,6-tetrahydro-α,4 dimethylfuro [4,3,2-ef][3]benzazepine-2-acetonitrile To a solution of lithium diisopropylamide (2.6 mmol) in tetrahydrofuran (20 ml) at −78° C. is added dropwise a solution of 7-chloro-3,4,5,6-tetrahydro-4-methylfuro-[4,3,2-ef][3]benzazepine-2-acetonitrile, prepared as in Example 33, in tetrahydrofuran (1 ml). After 0.5 hours, a solution of iodomethane (0.18 ml) in tetrahydrofuran (4 ml) is added. The resulting mixture is warmed to room temperature over 1.5 hours, quenched with ice water, and extracted with ethyl ether. The combined extracts are washed with water, dried over magnesium sulfate, filtered, and concentrated to give 7-chloro-3,4,5,6-tetrahydro-α, 4-dimethylfuro[4,3,2-ef][3]-benzazepine-2-acetonitrile.

EXAMPLE 36

7-Chloro-3,4,5,6-tetrahydro-8,4-dimethylfuro[4,3,2-ef]-[3]benzazepine-2-ethanamine To a suspension of lithium aluminum hydride (176 mmol) in anhydrous diethyl ether (200 ml) and tetrahydrofuran (50 ml) in an ice bath is added dropwise a solution of 7-chloro3,4,5,6-tetrahydro-α,4-dimethylfuro [4,3,2-ef]-[3]benzazepine-2-acetonitrile (44 mmol), prepared as in Example 36, in anhydrous diethyl ether (200 ml) and tetrahydrofuran (50 ml). The resulting suspension is stirred at reflux for 6 hours, and then water (7 ml), a solution of 10% sodium hydroxide (7 ml), and water (21 ml) are added sequentially. The mixture is diluted with ethyl ether (500 ml) and filtered. The filtrate is evaporated to give 7-chloro-3,4,5,6-tetrahydro-α,4-dimethylfuro-[4,3,2ef][3]benzazepine-2-ethanamine.

EXAMPLE 37

N-[2-(7-chloro-3,4,5,6-tetrahydro-4-methylfuro[4,3,2-ef]-[3]benzazepin 2-yl)propyl]benzenethanesulfonamide To a solution of 7-chloro-3,4,5,6-tetrahydro-α,4-dimethylfuro[4,3,2-ef][3]benzazepine-2-ethanamine 0 (1.5 mmol), prepared as in Example 37, and triethylamine (2.5 ml) in tetrahydrofuran (25 ml) at 5° C. is added slowly a solution of 2 phenethyl sulfonyl chloride (1.6 mmol) in tetrah.dyrofuran (2.5 ml). The resulting mixture is stirred for 2 hours at room temperature, poured into a cold solution of sodium bicarbonate (8 ml), and extracted with methylene chloride. The combined extracts are washed with water, saturated sodium chloride solution, and dried over magnesium sulfate. The residue obtained after evaporation is flash chromatographed to give N-[2-(7-chloro-3,4,5,6-tetrahydro-4-methylfuro[4,3,2-ef]-[3]benzazepin-2-yl)propyl]benzenesulfonamide.

EXAMPLE 38

7-Chloro-3,4,5,6-tetrahydro-N,N,4-trimethylfuro-[4,3,2-ef][3]benzazepine-2-methanamine To a solution of 7-chloro-3,4,5,6-tetrahydro- N,N,4-trimethylfuro [4,3,2-ef][3]benzazepine-2-carboxamide (9.4 mmol), prepared as in Example 4, in -tetrahydrofuran (20 ml) is added diborane (10 mmol). The mixture is refluxed for 3 hours, then treated with methanol (10 ml) and dilute hydrochloric acid (10 ml). The mixture is refluxed for 30 minutes and allowed to stir at room temperature overnight. A solid is filtered from the reaction mixture to give 7-chloro-3,4,5,6-tetrahydro-N,N,4-trimethylfuro-[4,3,2-ef][3]benzazepine-2-methanamine hydrochloride.

EXAMPLE 39

An oral dosage form for administering the presently invented compounds is produced by screening, mixing, and filling into a hard gelatin capsule ingredients in the proportions shown in Table II, below.

TABLE II

| Ingredients | Amounts |
|---|---|
| 2-[(N-Methyl-2-methylpropylsulfonamido)methyl]-7-chloro-3,4,5,6-tetrahydro-4-methylfuro[4,3,2-ef]-[3]benzazepine | 50 mg |
| magnesium stearate | 5 mg |
| lactose | 75 mg |

EXAMPLE 40

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
|---|---|
| 7-Chloro-3,4,5,6-tetrahydro-4-methylfuro[4,3,2,-ef][3]benzazepine-2-methanamine | 100 mg |
| calcium sulfate dihydrate | 150 mg |
| sucrose | 20 mg |
| starch | 10 mg |
| talc | 5 mg |

TABLE III-continued

| Ingredients | Amounts |
|---|---|
| stearic acid | 3 mg |

EXAMPLE 41

N-(7-Chloro-3,4,5,6-tetrahydro-4-methylfuro[4,3,2-ef]-[3]benzazepin-2-yl)methyl-3-phenylpropamide, 75 mg, is dispersed in 25 ml of normal saline to prepare an injectable preparation.

While the preferred embodiments of the invention are illustrated by the above, the invention is not limited to the precise instructions herein disclosed and that the right to all modifications coming within the scope of the following claims is reserved.

What is claimed is:

1. A compound of the formula:

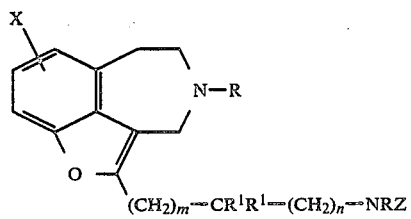

in which:

X is H, F, Cl, Br, I, CF$_3$, C$_{1-6}$alkyl, COR$^2$, CO$_2$R$^2$, CONR$^3$R$^3$, CN, NO$_2$, NR$^4$R$^1$, OR$^4$, SC$_{1-4}$alkyl, S(CH$_2$)$_{0-6}$Ph, SCF$_3$, or any accessible synthetically stable combination thereof of up to three substituents;

each R independently is H, C$_{1-6}$alkyl, or C$_{3-5}$alkenyl, except where the double bond is in the 1-position;

each R$^1$ independently is H or C$_{1-6}$alkyl;

Z is R, COR$^5$, CONR$^3$R$^6$, CO$_2$R$^8$, or SO$_2$R$^7$;

m an n are each 0 to 2, but m+n is not greater than 2;

each R$^2$ independently is C$_{1-6}$alkyl or (CH$_2$)$_{0-6}$Ph;

each R$^3$ independently is H, C$_{1-6}$alkyl, COR$^2$, or SO$_2$R$^2$;

R$^5$ is H, C$_{1-6}$alkyl, (CH$_2$)$_{0-6}$Ph, CH=CHPh, C$_{3-5}$alkenyl, (CH$_2$)$_{1-3}$OPh, (CH$_2$)$_{1-3}$SPh, or (CH$_2$)$_{1-3}$OR$^1$;

R$^6$ is H, C$_{1-6}$ alkyl, (CH$_2$)$_{0-6}$Ph, (CH$_2$)$_{2-3}$OPh, (CH$_2$)$_{2-3}$SPh, or (CH$_2$)$_{2-3}$OR$^1$;

R$^7$ is C$_{1-6}$alkyl, (CH$_2$)$_{0-6}$Ph, CH=CHPh, C$_{3-5}$alkenyl, (CH$_2$)$_{1-3}$OPh, (CH$_2$)$_{1-3}$SPh, or (CH$_2$)$_{1-3}$OR$^1$; and R$^8$ is C$_{1-6}$alkyl, (CH$_2$)$_{0-6}$Ph, (CH$_2$)$_{2-3}$OPh, (CH$_2$)$_{2-3}$SPh, or (CH$_2$)$_{2-3}$OR$^1$; or a pharmaceutically acceptable salt thereof.

2. A compound of claim 1 having the formula:

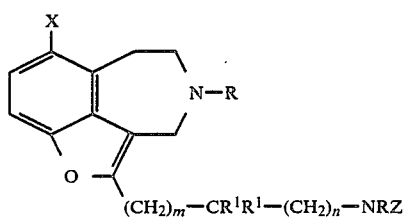

in which:

X is H, F, Cl, Br, I, CF$_3$, C$_{1-6}$alkyl, COR$^2$, CO$_2$R$^2$, CONR$^3$R$^3$, CN, NO$_2$, NR$^4$R$^1$, OR$^4$, SC$_{1-4}$alkyl, (CH$_2$)$_{0-6}$Ph, SCF$_3$, or any accessible synthetically stable combination thereof of up to three substituents;

each R independently is H, $C_{1-6}$alkyl, or $C_{3-5}$alkenyl, except where the double bond is in the 1- position;

each $R^1$ independently is H or $C_{1-6}$alkyl;

Z is R, $COR^5$, $CONR^3R^6$, $CO_2R^8$, or $SO_2R^7$;

m and n are each 0 to 2, but m+n is not greater than 2;

each $R^2$ independently is $C_{1-6}$alkyl or $(CH_2)_{0-6}Ph$;

each $R^3$ independently is H, $C_{1-6}$alkyl, or $(CH_2)_{0-6}Ph$;

each $R^4$ independently is H, $C_{1-6}$alkyl, $COR^2$, or $SO_2R^2$;

$R^5$ is H, $C_{1-6}$alkyl, $(CH_2)_{0-6}Ph$, $CH=CHh$, $C_{3-5}$alkenyl, $(CH_2)_{1-3}OPh$, $(CH_2)_{1-3}SPh$ or $(CH_2)_{1-3}OR^1$;

$R^6$ is H, $C_{1-6}$alkyl, $(CH_2)_{0-6}Ph$, $(CH_2)_{2-3}OPh$, $(CH_2)_{203}SPh$, or $(CH_2)_{2-3}OR^1$;

$R^7$ is $C_{1-6}$alkyl, $(CH_2)_{0-6}Ph$, $CH=CHPH$, $C_{3-5}$alkenyl, $(CH_2)_{1-3}OPh$, $(CH_2)_{1-3}SPH$, or $(CH_2)_{1-3}OR^1$; and $R^8$ is $C_{1-6}$alkyl, $(CH_2)_{0-6}Ph$, $(CH_2)_{2-3}OPh$, $(CH_2)_{2-3}SPH$, or $(CH_3)_{2-3}OR^1$; or a pharmaceutically acceptable salt thereof.

3. A compound of claim 2 wherein X is F, Cl, Br, or I.

4. A compound of claim 3 wherein R is $CH_3$.

5. A compound of claim 4 that is N-[(7-chloro-3,4,5,6-tetrahydro-4-methylfuro [4,3,2-ef][3]benzazepin-2-yl)methyl]-2-methylpropanesulfonamide.

6. A compound of claim 4 that is:
7-chloro-3,4,5,6-tetrahydro-4-methylfuro[4,3,2-ef]-[3]benzazepine-2-methanamine;
N-[(7-chloro-3,4,5,6-tetrahydro-4-methylfuro[4,3,2-ef]-[3]benzazepin-2-yl)methyl]benzenepropanamide;
N-[(7-chloro-3,4,5,6-tetrahydro-4-methylfuro[4,3,2-ef][3]benzazepin-2-yl)methyl]-2-phenoxyacetamide;
N-[(7-chloro-3,4,5,6-tetrahydro-4-methylfuro -[4,3,2-ef][3]benzazepin-2-yl)methyl]carbamic acid phenylmethyl ester;
N-[(7-chloro-3,4,5,6-tetrahydro-4-methylfuro -[4,3,2-ef][3]benzazepin-2-yl)methyl]carbamic acid ethyl ester;
N-[(7-chloro-3,4,5,6-tetrahydro-4-methylfuro -[4,3,2-ef][3]benzazepin-2-yl)methyl]-N-methyl-carbamic acid ethyl ester;
N-[(7-chloro-3,4,5,6-tetrahydro-4-methylfuro[4,3,2-ef]-[3]benzazepin-2-yl)methyl]propanamide;
N-[(7-chloro-3,4,5,6-tetrahydro-4-methylfuro[4,3,2-ef]-[3]benzazepin-2-yl)methyl]-N-methyl-propanamide; or
N-[(7-chloro-3,4,5,6-tetrahydro-4-methylfuro -[4,3,2-ef][3]benzazepin-2-yl)methyl]benzamide.

7. A pharmaceutical composition comprising an effective amount of a compound of claim 1 and a suitable pharmaceutical carrier.

8. A pharmaceutical composition of claim 7 wherein the compound is N-[(7-chloro-3,4,5,6-tetrahydro-4-methylfuro [4,3,2-ef][3]benzazepin-2-yl)methyl]-2-methylpropanesulfonamide.

9. A pharmaceutical composition of claim 7 wherein the compound is:
7-chloro-3,4,5,6-tetrahydro-4-methylfuro[4,3,2-ef]-[3]benzazepine-2-methanamine;
N-[(7-chloro-3,4,5,6-tetrahydro-4-methylfuro[4,3,2-ef]-[3]benzazepin-2-yl)methyl]benzenepropanamide;
N-[(7-chloro-3,4,5,6-tetrahydro-4-methylfuro[4,3,2-ef]-[3]benzazepin-2-yl)methyl]-2-phenoxyacetamide;
N-[(7-chloro-3,4,5,6-tetrahydro-4-methylfuro -[4,3,2-ef][3]benzazepin-2-yl)methyl]carbamic acid phenylmethyl ester;
N-[(7-chloro-3,4,5,6-tetrahydro-4 methylfuro -[4,3,2-ef][3]benzazepin-2-yl)methyl]carbamic acid ethyl ester;
N-[(7 chloro-3,4,5,6-tetrahydro-4-methylfuro -[4,3,2-ef][3]benzazepin-2-yl)methyl]-N-methyl-carbamic acid ethyl ester;
N-[(7-chloro-3,4,5,6-tetrahydro-4-methylfuro[4,3,2-ef]-[3]benzazepin-2-yl)methyl]propanamide;
N-[(7-chloro-3,4,5,6-tetrahydro-4-methylfuro[4,3,2-ef]-[3]benzazepin-2-yl)methyl]-N-methyl propanamide; or
N-[(7-chloro-3,4,5,6-tetrahydro-4-methylfuro - [4,3,2-ef][3]benzazepin-2-yl)methyl]benzamide.

10. A method of antagonizing α-adrenergic receptors in mammals that comprises administering to a subject in need thereof an effective amount of a compound of claim 1.

11. A method of claim 10 wherein the compound is N-[(7-chloro-3,4,5,6-tetrahydro-4-methylfuro[4,3,2-ef][3]-benzazepin-2-yl)methyl]-2-methylpropanesulfonamide.

12. A method of claim 10 wherein the compound is:
7-chloro-3,4,5,6-tetrahydro-4-methylfuro[4,3,2-ef]-[3]benzazepine-2-methanamine;
N-[(7-chloro-3,4,5,6-tetrahydro-4-methylfuro[4,3,2-ef]-[3]benzazepin-2-yl)methylbenzenepropanamide;
N-[(7-chloro-3,4,5,6-tetrahydro-4-methylfuro[4,3,2-ef]-[3]benzazepin-2-yl)methyl]-2-phenoxyacetamide;
N-[(7-chloro-3,4,5,6-tetrahydro-4-methylfuro -[4,3,2-ef][3]benzazepin-2-yl)methyl]carbamic acid phenylmethyl ester;
N-[(7-chloro-3,4,5,6-tetrahydro-4 methylfuro -[4,3,2-ef][3]benzazepin-2-yl)methyl]carbamic acid ethyl ester;
N [(7-chloro 3,4,5,6-tetrahydro-4-methylfuro -[4,3,2-ef][3]benzazepin-2-yl)methyl]-N-methyl-carbamic acid ethyl ester;
N-[(7-chloro-3,4,5,6-tetrahydro-4-methylfuro[4,3,2-ef]-[3]benzazepin-2-yl)methyl]propanamide;
N-[(7-chloro-3,4,5,6-tetrahydro-4-methylfuro[4,3,2-ef]-[3]benzazepin-2-yl)methyl]-N-methyl-propanamide; or
N-[(7-chloro-3,4,5,6-tetrahydro-4-methylfuro -[4,3,2-ef][3]benzazepin-2-yl)methyl]benzamide.

13. A method of reducing blood pressure in mammals that comprises administering to a subject in need thereof an effective amount of a compound of claim 1.

14. A method of treating cardiovascular diseases in mammals that comprises administering to a subject in need thereof an effective amount of a compound of claim 1.

15. A method of treating benign prostatic hypertrophy in mammals that comprises administering to a subject in need thereof an effective amount of a compound of claim 1.

16. A method of treating depression in mammals that comprises administering to a subject in need thereof an effective amount of a compound of claim 1.

17. A method of treating obesity in mammals that comprises administering to a subject in need thereof an effective amount of a compound of claim 1.

18. A method of treating diabetes in mammals that comprises administering to a subject in need thereof an effective amount of a compound of claim 1.

* * * * *

UNITED STATES PATENT AND TRADEMARK OFFICE
CERTIFICATE OF CORRECTION

PATENT NO. : 4,981,849
DATED : January 1, 1991
INVENTOR(S) : Thomas W. Ku

It is certified that error appears in the above-identified patent and that said Letters Patent is hereby corrected as shown below:

In Claim 1, column 24, line 42, after "$C_{1-6}$alkyl," insert --- or $(CH_2)_{0-6}$Ph; each $R^4$ independently is H, $C_{1-6}$alkyl, ---.

In Claim 2, column 25, line 13, replace "CH=CHh" with --- CH=CHPh ---.

In Claim 2, column 25, line 16, replace "$(CH_2)_{203}$SPH," with --- $(CH_2)_{2-3}$SPh, ---.

In Claim 2, column 25, line 20, replace "$(CH_2)_{2-3}$SPH," with --- $(CH_2)_{2-3}$SPh, ---.

Signed and Sealed this

Fourth Day of August, 1992

Attest:

DOUGLAS B. COMER

Attesting Officer

Acting Commissioner of Patents and Trademarks